US006629938B1

(12) United States Patent
Engvall et al.

(10) Patent No.: US 6,629,938 B1
(45) Date of Patent: Oct. 7, 2003

(54) APPARATUS FOR TREATMENT OF MÉNIERE'S DISEASE AND SIMILAR CONDITIONS

(75) Inventors: Daniel Engvall, Halmstad (SE); Anders Nilsson, Halmstad (SE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/743,168
(22) PCT Filed: Jun. 29, 1999
(86) PCT No.: PCT/SE99/01168

§ 371 (c)(1),
(2), (4) Date: Mar. 14, 2001

(87) PCT Pub. No.: WO00/01346

PCT Pub. Date: Jan. 13, 2000

(30) Foreign Application Priority Data

Jul. 6, 1998 (SE) .............................................. 9802423

(51) Int. Cl.[7] .............................................. A61H 23/00
(52) U.S. Cl. .......................... 601/76; 601/148; 600/559
(58) Field of Search .............................. 601/76, 77, 10, 601/148, 149; 600/559; 607/105

(56) References Cited

U.S. PATENT DOCUMENTS 6,159,171 A * 12/2000 Densert et al. ............... 601/76

FOREIGN PATENT DOCUMENTS

| GB | 10695 | 1/1909 |
|---|---|---|
| WO | 83/02556 | 8/1983 |
| WO | 93/08775 | 5/1993 |
| WO | 97/23178 | 7/1997 |

OTHER PUBLICATIONS

Preprint from Acta Otolaryngol (Stockh) 1986 "Transmission of Square Wave Pressure Pulses through the Perilymphatic Fluid in Cats", by B. Densert et al., pp. 1–8.

* cited by examiner

Primary Examiner—Danton D. DeMille
Assistant Examiner—Quang D Thanh
(74) Attorney, Agent, or Firm—Ostrolenk, Faber, Gerb & Soffen, LLP

(57) ABSTRACT

An apparatus for treatment of Ménière's disease by intermittently increasing air (gas) pressure, in an air (gas) pressure chamber in communication with an outwardly sealed external ear volume bordering the tympanic membrane, comprises a peripherally fixed flexible circular diaphragm forming a wall of the chamber and being displaceable in a perpendicular direction essentially without being tensioned. Displacement of the diaphragm away from the chamber is effected by air pressure built up in the chamber, not by a separate displacement device. The apparatus further comprises a linear electromagnetic device for displacing the diaphragm. The apparatus may include systems for gas pressure sensing; chamber pressure equalizing; and microprocessor control, for controlling the displacement of the diaphragm and the pressure equalizing device by a signal input from the pressure sensing device.

31 Claims, 3 Drawing Sheets

APPARATUS FOR TREATMENT OF MÉNIÈRE'S DISEASE AND SIMILAR CONDITIONS

FIELD OF THE INVENTION

The present Invention relates to an apparatus for treatment of Ménière's disease and similar conditions by producing variations in positive air pressure, which are transmitted to one of the ears of a patient.

BACKGROUND OF THE INVENTION

Ménière's disease can be treated by affecting the pressure in the internal ear, in particular the endolymphatic system.

WO 83/02556 discloses an apparatus for influencing the hydrodynamic system of the inner ear comprising a displaceable diaphragm forming the wall of an air pressure generating chamber, the diaphragm being reciprocally displaceable by means of a crank coupling in a direction away from the chamber against the force of a spring coil.

WO 93/08775 discloses an air pressure generator for the treatment of Ménière's disease by pressure pulses generated by a flexible membrane forming a wall in a pressure generating chamber, the membrane being displaced by actuation means rigidly coupled to the shaft of an electrical motor.

WO 97/23178 discloses a device for affecting the hydrodynamic system of the inner ear comprising first means for generating a static pressure level and second means for causing a variation of that level in accordance with a predetermined program controlled by a control unit. Each of the first and second means comprise a flexible membrane. Also in this known apparatus one half of the reciprocating movement of the diaphragm, the one in which the diaphragm moves towards the pressure generating chamber, is caused by spring means.

When applying square wave pulses to the internal ear in cats with a patent cochlear aqueduct a pronounced rebound effect could be noted (Transmission of Square Wave Pressure Pulses through the Perilymphatic Fluids in Cats, B. Densert et al., Acta Otolaryngol., Stockholm 1986). In humans the situation might be similar. The pressure changes in the internal ear caused by the application of square wave pulses according to methods disclosed in the prior art thus could lead to results substantially differing from what was endeavoured. This provides a possible explanation of the fact that, in spite of various apparatuses for the production and transmission of such air pressure pulses having been devised over the past fifteen years, none of them has been put into practical use at a commercial scale. This delay in the implementation of an interesting therapeutic principle seems to be due not only to these apparatuses having certain drawbacks from a constructional point of view, making them insufficiently adapted to the need of most out-patients, but also to methodological shortcomings in regard of how to vary the pressure during a treatment such as to make it applicable to a large group of patients.

OBJECTS OF THE INVENTION

The present invention seeks to overcome these drawbacks and problems, and to provide an improved apparatus for treating Ménière's disease and similar conditions.

Other objects of the invention will become apparent from the following short description of the invention and a preferred embodiment of it, as well as from the appended claims.

SUMMARY OF THE INVENTION

The present invention bases on the insight that the forced displacement of the diaphragm in both directions, that is, towards and away from the pressure generating chamber, carries with it a number of problems, and can be advantageously substituted by a forced movement towards the chamber and a passive movement away from the chamber. One drawback with the bi-directional forced movement is the marked deviation from linearity of the spring force; another is the substantial variation of spring force within a sample of coil springs of the same kind. The incremental spring force substantially increases with the distance of diaphragm's displacement from an idle position and translates into problems with the control of the device by the microprocessor. Another drawback with prior art devices is excess energy consumption caused by the need to work against an apparatus-inherent force in both directions of displacement.

According to the present invention is provided an apparatus for treatment of Ménière's disease by intermittently increasing, in an air (gas) pressure chamber being in communication with an outwardly sealed external ear volume bordering to the tympanic membrane, air (gas) pressure, the apparatus comprising a peripherally fixed flexible circular diaphragm forming a wall of the chamber and being displaceable (from an idle position) in the direction of the chamber, the apparatus further comprising actuating means for displacing the diaphragm in the direction of the chamber but essentially lacking means for displacing it in an opposite direction. The movement of the diaphragm away from the chamber thus is essentially caused by the air pressure built up in the chamber and cavities communicating with the chamber. By 'essentially' is meant that the generation of small resilient forces on displacement of the membrane (diaphragm) according to the invention towards the chamber in an open state is negligible in comparison with the resistance experienced in a corresponding displacement with the chamber in a closed state; in this context 'closed state' refers to the chamber being in communication with the the outwardly sealed external ear volume but not with the atmosphere, while 'open state' refers to the chamber being in communication with the outwardly sealed external ear volume and with the atmosphere, for instance by of an open valve.

By 'negligible' is meant that the force required to displace the diaphragm by a given distance, such as a distance of about 5 mm, towards the chamber with the chamber in a closed state is at least 5 times greater that the force required for a corresponding displacement with the chamber in an open state, preferably at least 10 times greater.

In other words, the design of the diaphragm should be adapted to avoid, up to the desired maximum displacement, the generation of substantial resilient forces. It is thus preferred for the diaphragm to be displaceable (from an idle, neutral position) towards the chamber essentially without being tensioned.

It is also important that combined mass of the displaceable elements of the apparatus of the invention, that is, the diaphragm and the elements coupled to the diaphragm to make it move towards the chamber, is kept as small as possible. This contributes to the apparatus of the invention saving energy in comparison with devices known in the art which is of advantage in particular for battery driven mobile apparatus.

Preferably the actuating means comprise linear electromagnetic displacement means.

According to a first preferred aspect of the invention the apparatus comprises one or several or: pressure sensing means for monitoring the gas pressure in the chamber; pressure equalising means for equalising the air pressure in the chamber with ambient air pressure; control means comprising a microprocessor, for controlling the displacement of the diaphragm and the pressure equalising means by signal input from the pressure sensing means.

It is preferred for the pressure equalising means to comprise valve means. It is preferred for the valve means to be in an open (equalising) position except during the generation of pulse trains. Particularly preferred are silent valve means working below a sound pressure level of 20 dB, in particular valve means provided with sealing faces comprising a resilient polymer. Also preferred is to control the pressure equalising means in a way such as to reduce valve noise, in particular by opening the valve slowly at the end of a pulse train and closing the valve slowly before the start of a pulse train, for example by making the opening and closing to comprise from about 0.5 seconds to 1.5 seconds, typically about one second, when going from the fully closed position to the fully opened position and vice-versa.

It is preferred for the diaphragm actuating means to comprise an elongate actuating member having an axis and being fixed to the diaphragm at its one end and, preferably at its other end, to a ferromagnetic core, an electric coil (solenoid) for displacement of the core along said axis in the direction of the chamber; means for energising the coil controlled by the control means. These diaphragm actuating means thus displace the diaphragm by a linear unidirectional force caused by an electromagnet. The coil is energised by pulse modulated 0–12 V DC. The voltage/generated force (pressure) ratio of the coil, that is, the coil voltage/ diaphragm displacement ratio is about constant within the working range of the invention. The same is true for the pressure/diaphragm displacement ratio.

According to a second preferred aspect of the invention the pressure in the pressure chamber is increased from ambient pressure ($p_0$) to a first level ($p_1$) above ambient pressure and from there ($p_1$) repeatedly increased to a second level ($P_2$) and decreased to the first level ($p_1$) again, and, following said repeated increase and decrease, the pressure is decreased from the first level ($p_1$) to ambient pressure ($p_0$). Preferably $p_1$ is from 4 to 16 cm $H_2O$, $P_2$ is from 8 to 16 cm $H_2O$, with the proviso that $p_1<P_2$, the pressure increase rate is from 0 to 4 mm $H_2O$ per millisecond, the pressure decrease rate is from 0 to 2 mm $H_2O$ per millisecond, the modulation frequency is from 3 to 9 Hz, preferably from 5 to 7 Hz, most preferred about 6 Hz, the intermittent time period being from 3 to 10 seconds, preferably about 5 seconds. It is also preferred to administer, during a treatment session, two to four treatments, in particular three treatments, separated by from about 25 seconds to about 90 seconds.

To prevent the pressure to rise excessively in case of a software failure the inclusion of a hardware controlled extra safety means is preferred, breaking the current to the pressure equalising means and the pressure actuating means if the pressure in the chamber is in excess of ambient pressure by about 25 cm $H_2O$.

On the other hand it is important not to apply a pressure which would expose inner ear structures to suction, that is, negative pressure. It is therefore preferred to provide the apparatus of the invention with a mechanical safety valve for protection of the patient against negative pressure opening at a pressure of about −1 cm $H_2O$; the acceptance of a slightly negative pressure is due to design requirements for such a mechanical safety valve. It is also preferred to provide the apparatus of the invention with a safety valve for protection of the patient against positive pressure opening at a pressure of about +35 cm $H_2O$. Both safety valves are purely mechanical and not controlled by the control means.

The combined volume of the chamber and the conduit can be varied within a broad range but considerations of design and conditions of use suggest the combined volume to be preferably from about 20 cm$^3$ to about 50 cm$^3$. It is important to adapt the effective area of the diaphragm to the combined volume and the outwardly sealed ear volume so as to keep its displacement below 5 mm, preferably within a range (working range) of below 3 mm for effecting the pressure variations according to the invention; this includes potential extra displacement caused by minor leakage which the apparatus is able to compensate for, and by the compliance of tissues bordering to the outwardly sealed ear volume. Typically the effective diaphragm area is in the range of from about 3 to about 8 cm$^2$. For a combined volume of 30 cm$^3$ an effective diaphragm area of 5 cm$^2$ was found to be appropriate. 'Effective diaphragm area' is the area of the displaceable portion of the diaphragm 4, including its central portion 32 clamped between elements 35,36.

According to a preferred aspect of the invention it is preferred to store, in an E$^2$PROM (electrically erasable and programmable read-only memory) or a functionally equivalent device coupled to the microprocessor, the information for control of the apparatus in form of parameter sets, each set comprising all parameters necessary to carry out a treatment, that is, the variation of pressure in the chamber with time during treatment. It is preferred to provide the apparatus of the invention with input means to allow a parameter set to be replaced by another set. Input means not requiring an electrical connection, such as infrared (IR) input means, are preferred. The various parameter sets are stored in a computer, for instance a PC, and transferred therefrom to the apparatus of the invention. It is also preferred to store several parameter sets in the E$^2$PROM or a functionally equivalent device, and to provide the apparatus with means for their individual selection. Thus the software for controlling the apparatus invention comprises a fixed portion stored in the PROM of the microprocessor and an exchangeable portion stored in an E$^2$PROM or other suitable storage medium.

In the following the invention will be explained in more detail by reference to a preferred embodiment illustrated in a drawing. The embodiment is however only provided as an example and must not be considered to limit the invention in any way.

SHORT DESCRIPTION OF THE DRAWING

Figure 1:
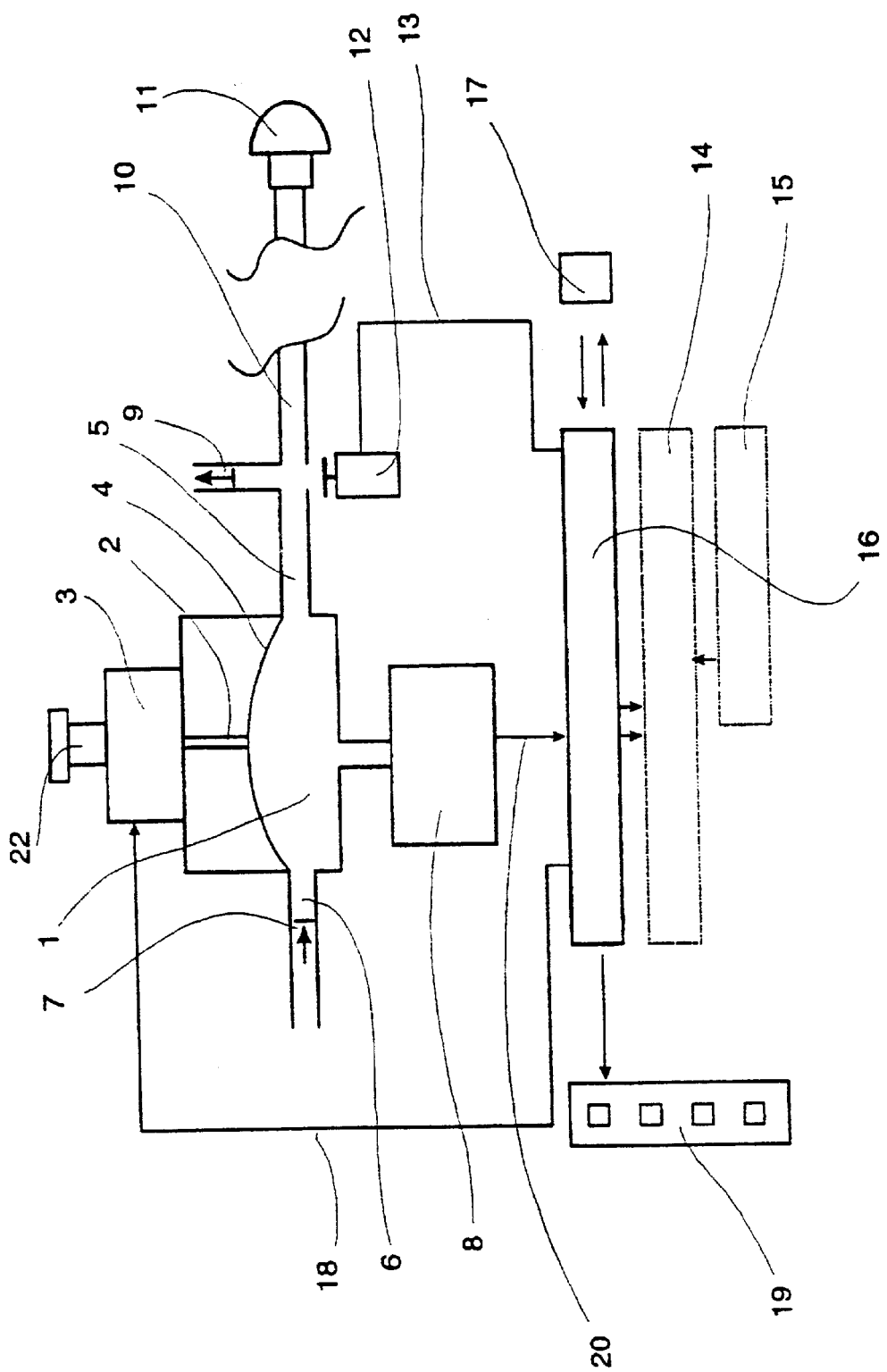
FIG. 1 is a schematic function diagram of an apparatus according to the invention.

A preferred embodiment of the apparatus according to the present invention is illustrated schematically in FIG. 1. It comprises a generally cylindrical chamber 1 for generating pressure pulses by displacement of a flexible circular rubber diaphragm (membrane) 4 forming one base of the chamber 1, a piston 2 centrally fixed to the essentially non-tensioned (the state of tension being not evident from FIG. 1) diaphragm 4 at its one end and at a ferromagnetic alloy core 22 at its other end, the core 22 being partially inserted into a field coil (solenoid) 3 at the idle (non-pressurised) position. The chamber 1 has a terminal section 5 provided with a 'silent' (sound pressure level <20 dB) on/off electromagnetic equalising valve 12 which puts it in communication with the atmosphere when in an open position.

Figure 3:
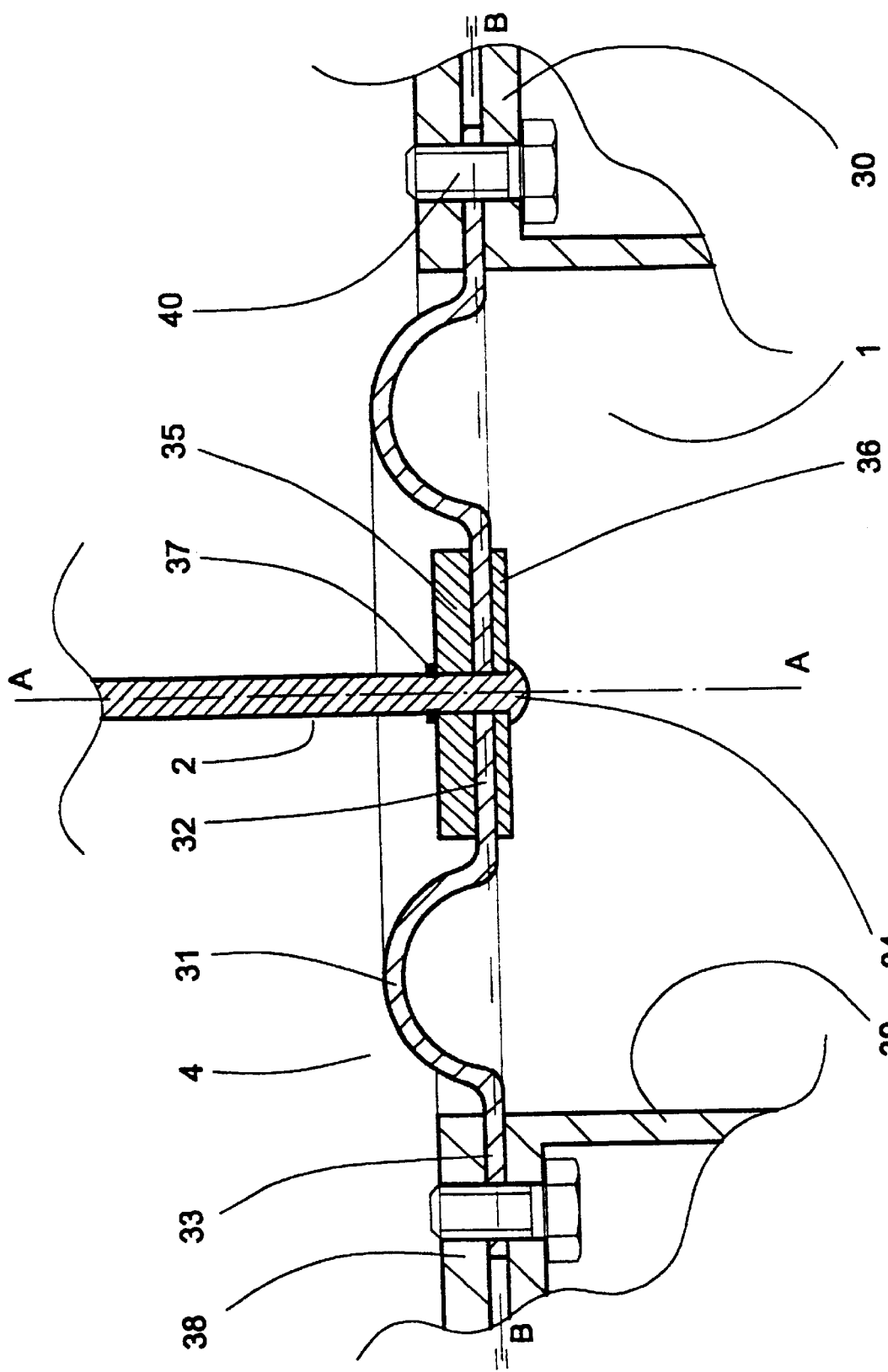
FIG. 3 shows a circular diaphragm of the invention in a mounted state, in a section perpendicular to the plane of the diaphragm B-B and through tIAs centre along axis A—A.

A diaphragm 4 of the specific design according to the invention is shown in FIG. 3. The diaphragm 4 consists of a flat circular central portion 32 and a flat annular peripheral portion 33 linked by an annular portion 31 which is approximately semicircular in radial section; it is also possible to use, for instance, a diaphragm having several radially spaced annular portions 31 similar to a circular wave arising at one point at the surface of a liquid. The flat portions 32, 33 define the diaphragm plane B—B. The semicircular portion 31 allows the diaphragm 4 to be displaced along axis A—A out of the diaphragm plane B-B in a forward (towards the chamber) axial direction; displacement is effected against resilient deformation forces in the diaphragm which however are insignificant in relation to resistance against compression by the air enclosed in the chamber. The flat circular portion 32 is clamped between upper and lower circular disks 35, 36. The circular portion 32 and the upper and lower disks 35, 36 have central bores for mounting on the piston 2 provided with a roundhead 34 against which they are secured by a circlip 37 disposed in a peripheral slot of the piston 2. At its other end (not shown) the piston 2 is fixed to a soft iron or ferromagnetic alloy core 22 (see FIG. 1) partially inserted into the lumen of the field coil 3 (see FIG. 1) at the coil end facing away from the diaphragm. The piston 2 thus extends into the coil from the other end of the coil. When the coil is energised the core 22 is drawn into the coil 3, that is, is displaced in the direction of the diaphragm 4. By means of a number of screws 40 the peripheral diaphragm section 33 is clamped between radially extending portions 38, 30 of the housing and the structure formning the cylindrical wall 39 of the chamber 1 for the generation of pressure pulses, respectively.

In the following the design and function of the preferred embodiment of the invention will be explained by reference to FIGS. 1 and 3. Via a flexible plastic tube 10 (of polystyrene, polypropylene or a similar material) the chamber 1 is put into communication with an air volume in the external ear bordering to the tympanic membrane of a patient sealed off by an ear plug 11. The tympanic membrane is penetrated by a microtube which has been applied by surgery; thereby the external and middle ear of the patient are put into communication. The pressure in the chamber 1 is monitored by a pressure sensor 8, the signal 20 of which is processed in a control unit comprising a microprocessor 16 and software 14. By input of sets of data 15 software parameters relating to pressure and time can be changed in an E$^2$PROM 19 coupled to the microprocessor. Input is via an IR-link 17 from data stored in a personal computer. One output signal 18 from the microprocessor 16 controls the power supplied to the field coil 3 while another output signal 13 controls the equalising value 12 by switching it between an open and a closed position. If, for some reason, the chamber 1 pressure cannot be maintained within the physiologically acceptable interval the equalising valve is opened. If the chamber pressure exceeds ambient pressure by 25 cm H$_2$O a hardware controlled safety function breaks the power both to the equilibrating valve 12 and the field coil 3. As a further safety precaution mechanical safety valves 7, 9 against negative pressure (opening pressure −1cm H$_2$O) and excess positive pressure, respectively, are provided in addition.

The treatment data are stored in the E$^2$PROM in form of one or several parameter sets. A parameter set contains all information in regard of pulse amplitude, frequency, pressure increase and decrease rate, etc. In addition each parameter set comprises data for the software controlled safety functions.

Figure 2:
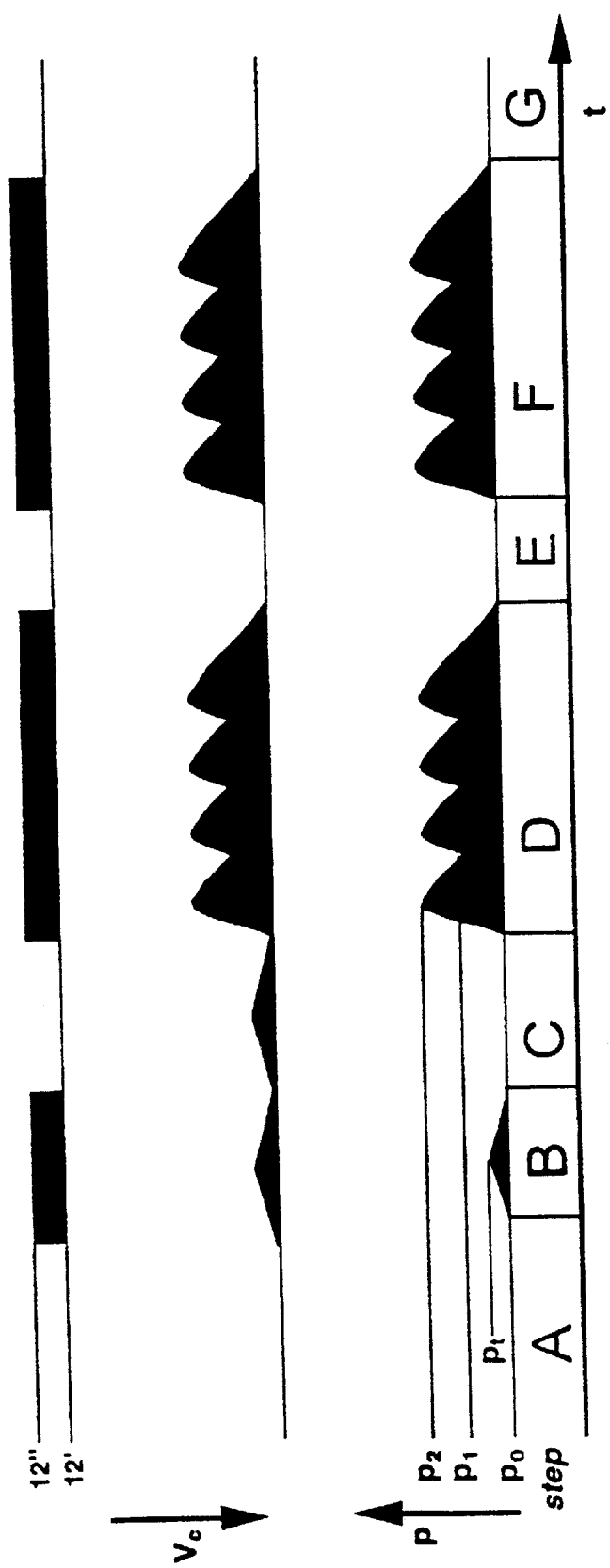
FIG. 2 is a schematic pulse diagram with a non-linear time axis.

In FIG. 2 a typical treatment sequence is shown, except for the number of pulse trains being reduced to two for the sake of simplicity. The chamber pressure (lowermost section of the diagram), the chamber volume (central section of the diagram) and the mode of the equalising valve 12 (uppermost section of the diagram; 12'=open; 12"=closed) are set off against time.

The various phases of the treatment sequence are identified by capital letters. During phase A the pressure sensor 8 is brought to a working temperature, the equilibrating valve 12 is in an open position, and the chamber 1 is at ambient pressure. Then follows a leak test in test phase B. During phase B the valve 12 is kept closed while the pressure is gradually increased to a test pressure $p_t$ of about 1 cm H$_2$O, and then again decreased to zero. In test phase C a test for openness is carried out. The chamber 1 volume $V_0$ is varied in the same way as in phase B but with valve 12 in an open position. If the test pressure $p_t$ deviates from the expected values the program will stop the apparatus from proceeding to the treatment sequence proper. During the first treatment phase D the chamber pressure p is gradually raised to an intermediate pressure $p_1$ and from there to the maximum pressure $p_2$, followed by a decrease to the intermediate pressure $p_1$; the $p_1 \rightarrow P_2 \rightarrow P_1$ cycle is repeated trice, followed by lowering the pressure to ambient pressure $P_0$. After an interval E of about 5 seconds a second pulse train (phase F) similar to the one in phase D is generated. This is followed by a second interval at $p_0$ (phase G) and 10 to 30 further pulse trains (not shown) with corresponding intervals. This first treatment section of equally spaced 12–32 pulse trains is followed by a rest period of about 25–90 seconds, and second and third treatment sections also spaced by a corresponding rest period. For optimal effect the treatment should be repeated several times a day.

What is claimed is:

1. An apparatus for treatment of Ménière's disease by intermittently increasing air (gas) pressure, in an air (gas) pressure chamber being in communication with an outwardly sealed external ear volume bordering to the tympanic membrane, the apparatus comprising a flexible diaphragm forming a wall of the chamber and being displaceable in the direction toward the chamber, the apparatus further comprising an actuator which when actuated displaces the diaphragm in the direction toward the chamber and when not actuated, passively permits the diaphragm to displace in an opposite direction.

2. The apparatus of claim 1, wherein the actuator comprises a linear electromagnetic device.

3. The apparatus according to claim 2, wherein the diaphragm actuator comprises an elongate actuating member having an axis and being fixed to the diaphragm at its one end and to a core of a ferromagnetic magnetic material; and an electric coil for displacement of the core along said axis in the direction toward the chamber.

4. The apparatus of claim 1, further comprising:
   a pressure sensor for monitoring pressure in the chamber;
   a pressure equalising conduit for equalising the pressure in the chamber with ambient air pressure; and
   a control system comprising a microprocessor, for controlling the displacement of the diaphragm and the pressure equalising conduit by a signal input from the pressure sensor.

5. The apparatus of claim 4, wherein the pressure equalising conduit comprises a valve.

6. The apparatus of claim 5, wherein the valve is in an open position except during the generation of said signal.

7. The apparatus of claim 5, further comprising a safety circuit for breaking the current to the pressure equalising valve and the actuator if the pressure exceeds ambient pressure by 25 cm $H_2O$ or more.

8. The apparatus of claim 4, wherein the diaphragm actuator comprises an elongate actuating member having an axis and being fixed to the diaphragm at its one end and to a core of a ferromagnetic magnetic material; an electric coil for displacement of the core along said axis in the direction of the chamber; and a device for energising the coil controlled by the control system.

9. The apparatus of claim 4, wherein the pressure equalising conduit comprises an on/off valve working at below a sound pressure level of 20 dB.

10. The apparatus of claim 9, wherein the valve is provided with sealing faces comprising a resilient polymer.

11. The apparatus of claim 9, wherein the valve is controlled to open, at the end of said signal, during from about 0.5 seconds to 1.5 seconds, preferably during about one second, from a fully closed position to a fully opened position.

12. The apparatus of claim 9, wherein the valve is controlled to be in an open position except during the generation of said signal.

13. The apparatus of claim 4, wherein variable information for control of the apparatus is stored in a storage medium associated with said microprocessor in the form of a parameter set in an $E^2PROM$ or other suitable storage medium.

14. The apparatus of claim 13, wherein the storage medium is associated with an input device with which a parameter set is replaceable by another parameter set.

15. The apparatus of claim 14, wherein the input device comprises an IR input device.

16. The apparatus according to claim 4, wherein the pressure equalising conduit comprises a valve.

17. The apparatus according to claim 16, wherein the valve is controlled to open, at the end of said signal, during from about 0.5 seconds to 1.5 seconds, preferably during about one second, from a fully closed position to a fully opened position.

18. The apparatus according to claim 16, wherein the valve is controlled to be in an open position except during the generation of said signal.

19. The apparatus of claim 1, comprising a mechanical safety valve for protection of the patient against negative pressure.

20. The apparatus according to claim 1, wherein the force required to displace the diaphragm by a given distance with said air (gas) pressure chamber in a closed state is five or more times greater than the force required for a corresponding displacement with the chamber in an open state.

21. The apparatus according to claim 20, wherein the force required to displace the diaphragm by a given distance with said air (gas) pressure chamber in a closed state is ten or more times greater than the force required for a corresponding displacement with the chamber in an open state.

22. The apparatus according to claim 20, wherein the displacement is about 3 mm.

23. The apparatus according to claim 21, wherein the displacement is about 3 mm.

24. The apparatus according to claim 1, wherein the diaphragm is displaceable in the direction toward the chamber substantially without being tensioned.

25. The apparatus according to claim 1, wherein the displacement of the diaphragm is below 5 mm, said displacement defining the working range of the apparatus.

26. The apparatus according to claim 25, wherein a chamber pressure/diaphragm displacement ratio is about constant within the working range of the apparatus.

27. The apparatus according to claim 25, wherein a coil voltage/diaphragm displacement ratio is about constant within the working range of the invention.

28. The apparatus according to claim 1, wherein a displacement of the diaphragm is below 3 mm, said displacement defining the working range of the apparatus.

29. The apparatus according to claim 28, wherein a chamber pressure/diaphragm displacement ratio is about constant within the working range of the apparatus.

30. The apparatus according to claim 28, wherein a coil voltage/diaphragm displacement ratio is about constant within the working range of the invention.

31. The apparatus according to claim 1, wherein the diaphragm actuator comprises an elongate actuating member having an axis and being fixed to the diaphragm at its one end and to a core of a ferromagnetic magnetic material; and an electric coil for displacement of the core along said axis in the direction toward the chamber.

\* \* \* \* \*